United States Patent
Kohara et al.

(10) Patent No.: US 10,443,526 B2
(45) Date of Patent: Oct. 15, 2019

(54) AIR-FUEL RATIO SENSING DEVICE

(71) Applicant: DENSO CORPORATION, Kariya, Aichi-pref. (JP)

(72) Inventors: Tomohiro Kohara, Kariya (JP); Yoshiyuki Kawase, Kariya (JP); Kazunori Kurokawa, Kariya (JP)

(73) Assignee: DENSO CORPORATION, Kariya (JP)

( * ) Notice: Subject to any disclaimer, the term of this patent is extended or adjusted under 35 U.S.C. 154(b) by 260 days.

(21) Appl. No.: 15/670,037

(22) Filed: Aug. 7, 2017

(65) Prior Publication Data

US 2018/0073456 A1    Mar. 15, 2018

(30) Foreign Application Priority Data

Sep. 14, 2016 (JP) .................. 2016-179789
Jun. 7, 2017 (JP) .................. 2017-112957

(51) Int. Cl.
*F02D 41/14* (2006.01)
*G01N 27/12* (2006.01)
*F02D 41/28* (2006.01)

(52) U.S. Cl.
CPC ..... *F02D 41/1456* (2013.01); *F02D 41/1495* (2013.01); *G01N 27/122* (2013.01); *F02D 2041/281* (2013.01)

(58) Field of Classification Search
CPC ............ F02D 31/1456; F02D 31/1495; F02D 2041/281; G01N 27/122
See application file for complete search history.

(56) References Cited

U.S. PATENT DOCUMENTS

| | | | | |
|---|---|---|---|---|
| 4,121,548 A * | 10/1978 | Hattori | ................ | F02D 41/1441 123/479 |
| 4,149,408 A * | 4/1979 | Ezoe | ................... | F02D 41/1495 73/114.72 |
| 4,166,380 A * | 9/1979 | Batz | ..................... | G01N 27/122 340/634 |
| 4,178,793 A * | 12/1979 | Bremer | ............... | F02D 41/1494 123/688 |
| 4,306,444 A * | 12/1981 | Hattori | ................. | G01N 27/122 123/694 |
| 4,324,218 A * | 4/1982 | Hattori | ................. | G01N 27/122 123/695 |

(Continued)

FOREIGN PATENT DOCUMENTS

| | | | | |
|---|---|---|---|---|
| JP | 61126458 A | * | 6/1986 | .......... G01N 27/122 |
| JP | H1-230931 A | | 8/1999 | |
| JP | 2000-081414 A | | 3/2000 | |

*Primary Examiner* — David J Bolduc
(74) *Attorney, Agent, or Firm* — Posz Law Group, PLC (57) ABSTRACT

An air-fuel ratio sensing device includes a resistor, an A/D converter, a parallel circuit unit, a second switch, a controlling unit, an air-fuel ratio sensing unit, and a deterioration sensing unit. The controlling unit controls to turn off the first switch and controls to turn on the second switch in a first interval, and the controlling unit controls to turn on the first switch and controls to turn off the second switch in a second interval. The air-fuel ratio sensing unit senses an air-fuel ratio based on a converting result of the A/D converter in the first interval. The deterioration sensing unit compares a reference value with a value obtained based on the converting result and senses a deterioration generated in the current sensing circuit unit in the second interval.

7 Claims, 6 Drawing Sheets

(56) References Cited

U.S. PATENT DOCUMENTS

| | | | | |
|---|---|---|---|---|
| 4,344,317 A * | 8/1982 | Hattori | F02D 41/1455 | 123/693 |
| 4,951,632 A * | 8/1990 | Yakuwa | F02D 41/1495 | 123/688 |
| 4,992,965 A * | 2/1991 | Holter | B60H 1/008 | 165/269 |
| 5,285,762 A * | 2/1994 | Werner | F02D 41/1479 | 123/690 |
| 6,034,610 A * | 3/2000 | Schnaibel | F02B 39/16 | 340/635 |
| 6,120,677 A * | 9/2000 | Yamada | G01N 27/4065 | 204/408 |
| 6,449,944 B1 * | 9/2002 | Yasui | F01N 11/007 | 60/274 |
| 8,393,316 B2 * | 3/2013 | Kunihiro | F01N 3/0842 | 123/697 |
| 2004/0222094 A1 * | 11/2004 | Ieda | F02D 41/1495 | 204/424 |
| 2005/0230248 A1 * | 10/2005 | Kawase | G01N 27/4175 | 204/424 |
| 2006/0157348 A1 * | 7/2006 | Inoue | F02D 41/1494 | 204/401 |
| 2006/0219555 A1 * | 10/2006 | Inagaki | F02D 41/1443 | 204/426 |
| 2007/0284248 A1 * | 12/2007 | Kawase | F02D 41/1454 | 204/424 |
| 2008/0196490 A1 * | 8/2008 | Fukagai | F02D 41/1456 | 73/114.72 |
| 2009/0038289 A1 * | 2/2009 | Oh-Hori | G01N 27/122 | 60/285 |
| 2009/0084172 A1 * | 4/2009 | Fukagai | F02D 41/1456 | 73/114.72 |
| 2011/0199709 A1 * | 8/2011 | Ieda | F02D 41/1494 | 361/78 |
| 2012/0266657 A1 * | 10/2012 | Barnikow | G01N 27/4065 | 73/31.05 |
| 2012/0273369 A1 * | 11/2012 | Kato | F02D 41/1454 | 205/775 |
| 2013/0180853 A1 * | 7/2013 | Mori | F02D 41/1455 | 204/406 |
| 2013/0192210 A1 * | 8/2013 | Nakano | F02D 41/1439 | 60/276 |
| 2013/0206596 A1 * | 8/2013 | Katsurahara | G01N 27/407 | 204/424 |
| 2013/0219984 A1 * | 8/2013 | Paggel | F02D 41/1495 | 73/1.06 |
| 2015/0041320 A1 * | 2/2015 | Yamada | F02D 41/1495 | 204/427 |
| 2015/0041334 A1 * | 2/2015 | Matsuoka | F02D 41/1454 | 205/775 |
| 2015/0323493 A1 * | 11/2015 | Uemura | F02D 41/28 | 204/406 |
| 2016/0123262 A1 * | 5/2016 | Matsuoka | F02D 41/123 | 73/1.06 |
| 2016/0202210 A1 * | 7/2016 | Nakata | G01N 27/4065 | 204/401 |
| 2017/0342933 A1 * | 11/2017 | Kamiya | F02D 41/021 | |
| 2018/0196101 A1 * | 7/2018 | Qu | G01R 31/2829 | |

* cited by examiner

AIR-FUEL RATIO SENSING DEVICE

CROSS REFERENCE TO RELATED APPLICATION

This application is based on Japanese Patent Application No. 2016-179789 filed on Sep. 14, 2016 and Japanese Patent Application No. 2017-112957 filed on Jun. 7, 2017, the disclosures of which are incorporated herein by reference.

TECHNICAL FIELD

The present disclosure relates to an air-fuel ratio sensing device.

BACKGROUND

JPH11-230931A discloses an air-fuel ratio sensing device including a resistor used to sense a current and an air-fuel ratio sensor. In this case, the resistor and the air-fuel ratio sensor constitute a series circuit. The air-fuel ratio sensing device further includes an A/D converter and a microcomputer. A voltage between two ends of the resistor is A/D converted by the A/D converter. The microcomputer senses an air-fuel ratio based on a converting result of the A/D converter.

SUMMARY

When a deterioration such as a time deterioration is generated in a current sensing circuit unit constituted by the resistor and the A/D converter, an error between a sensor current sensed by the microcomputer and a sensor current actually flowing through the air-fuel ratio sensor is generated. In this case, the sensor current sensed by the microcomputer indicates the converting result of the A/D converter. In the air-fuel ratio sensing device, when the deterioration is generated, a sensing of the air-fuel ratio is executed while the error is generated, and an environment load increases.

It is an object of the present disclosure to provide an air-fuel ratio sensing device which can suppress an increase of an environment load.

According to an aspect of the disclosure, the air-fuel ratio sensing device includes a resistor, an A/D converter, a parallel circuit unit, a second switch, a controlling unit, an air-fuel ratio sensing unit, and a deterioration sensing unit.

The resistor is connected with an air-fuel ratio sensor in a series connection, and the resistor and the air-fuel ratio sensor constitute a series circuit.

The series circuit has a first end portion and a second end portion.

The A/D converter A/D converts a voltage between two ends of the resistor, and the A/D converter and the resistor constitute a current sensing circuit unit.

The parallel circuit unit is connected with the resistor in a parallel connection, and includes a first switch and a constant current source which are connected with each other in a series connection.

The second switch is arranged between the resistor and the air-fuel ratio sensor.

The controlling unit controls to turn off the first switch to make the constant current source and the resistor be in a blocking state and controls to turn on the second switch to make the resistor and the air-fuel ratio sensor be in a conduction state in a first interval, and the controlling unit controls to turn on the first switch to make the constant current source and the resistor be in a conduction state and controls to turn off the second switch to make the resistor and the air-fuel ratio sensor be in a blocking state in a second interval that is different from the first interval.

The air-fuel ratio sensing unit senses an air-fuel ratio based on a converting result of the A/D converter in the first interval.

The deterioration sensing unit compares a reference value that is previously stored with a value obtained based on the converting result of the A/D converter and senses a deterioration generated in the current sensing circuit unit in the second interval.

According to the air-fuel ratio sensing device, the first switch is turned off and the second switch is turned on in the first interval, and the first switch is turned on and the second switch is turned off in the second interval. Thus, in the second interval, the constant current source is electrically connected with the resistor, and a constant current flows through the resistor. When a deterioration is generated in a current sensing circuit unit constituted by the resistor and the A/D converter, the value obtained based on the converting result of the A/D converter in the second interval changes. Thus, it can be sensed that the deterioration is generated in the current sensing circuit unit, by comparing the reference value with the value obtained based on the converting result of the A/D converter. Thus, it can be suppressed that the deterioration is ignored, and it can be suppressed that an environment load increases.

BRIEF DESCRIPTION OF THE DRAWINGS

The above and other objects, features and advantages of the present disclosure will become more apparent from the following detailed description made with reference to the accompanying drawings. In the drawings.

DESCRIPTION OF EMBODIMENTS

Embodiments of the present disclosure will be described hereafter referring to drawings. In the embodiments, a part that corresponds to a matter described in a preceding embodiment may be assigned with the same reference numeral.

First Embodiment

Figure 1:
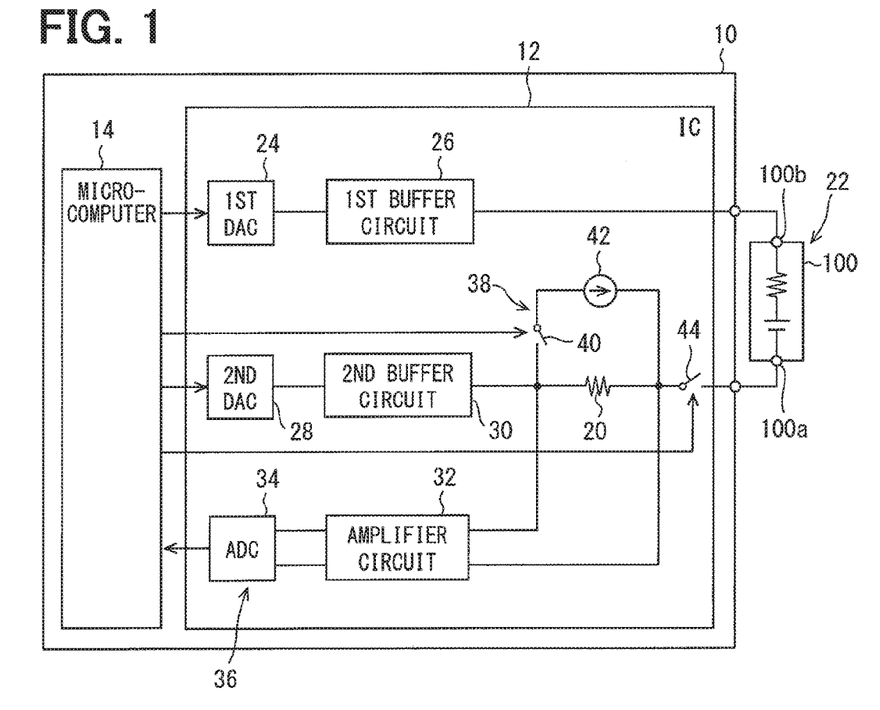
FIG. 1 is diagram showing an outline of an engine ECU to which an air-fuel ratio sensing device is applied, according to a first embodiment of the present disclosure.

Referring to FIG. 1, an engine electronic control unit (engine ECU) 10 to which an air-fuel ratio sensing device is applied according to a first embodiment of the present disclosure will be described. Hereafter, the air-fuel ratio sensing device will also be described.

As shown in FIG. 1, the engine ECU 10 is connected with an air-fuel ratio sensor 100 that senses an air-fuel ratio (A/F ratio).

The air-fuel ratio sensor 100 is arranged in an exhaust passage of an engine of a vehicle. The air-fuel ratio sensor 100 can be a lamination air-fuel ratio sensor that is of a limiting current type. When a voltage is applied to the air-fuel ratio sensor 100, the air-fuel ratio sensor 100 generates a limiting current according to the air-fuel ratio in an exhaust gas. The limiting current is a sensor current that is a current of the air-fuel ratio sensor 100 and is obtained according to the air-fuel ratio sensed by the air-fuel ratio sensor 100.

The engine ECU 10 includes an integrated current (IC) 12 and a microcomputer 14. The IC 12 includes a resistor 20, a first D/A converter (first DAC) 24, a second D/A converter (second DAC) 28, a first buffer circuit 26, a second buffer circuit 30, an amplifier circuit 32, an A/D converter 34, a parallel circuit 38, and a second switch 44.

The resistor 20 is connected with the air-fuel ratio sensor 100 in a series connection. The resistor 20 is a current sensing resistor that is used to sense the sensor current flowing through the air-fuel ratio sensor 100. When the air-fuel ratio sensor 100 is connected with the engine ECU 10, the resistor 20 and the air-fuel ratio sensor 100 constitute a series current 22. According to the present embodiment, a first end of the resistor 20 is connected with a first terminal 100a of the air-fuel ratio sensor 100 that is a negative terminal of the air-fuel ratio sensor 100.

The first D/A converter 24 applies a first voltage V1 to a first end portion of the series current 22. The first D/A converter 24 is equivalent to a first voltage applying unit. The first D/A converter 24 is connected with the series current 22 through the first buffer circuit 26. The first voltage V1 outputted by the first D/A converter 24 is determined according to an instruction signal of the microcomputer 14. According to the present embodiment, the first D/A converter 24 applies the first voltage V1 to the first end portion of the series current 22 that is closer to the air-fuel ratio sensor 100 than a second end portion is. The first D/A converter 24 is connected with a second terminal 100b of the air-fuel ratio sensor 100 that is a positive terminal of the air-fuel ratio sensor 100. The first D/A converter 24 outputs a DC voltage that is a constant voltage as the first voltage V1.

The first buffer circuit 26 includes an operational amplifier, and outputs a voltage from an output terminal of the first buffer circuit 26 that is the same as a voltage received by the first buffer circuit 26. The first buffer circuit 26 outputs the first voltage V1 to the second terminal 100b.

The second D/A converter 28 applies a second voltage V2 that is different from the first voltage V1 to a second end portion of the series current 22. The second D/A converter 28 is equivalent to a second voltage applying unit. Further, the second D/A converter 28 is equivalent to a voltage applying unit that applies a voltage to an end portion of the series current 22 that is closer to the resistor 20 than the other end portion of the series current 22 is. In this case, the voltage applying unit is one of the first voltage applying unit and the second voltage applying unit. The second D/A converter 28 is connected with the series current 22 through the second buffer circuit 30. The second voltage V2 outputted by the second D/A converter 28 is determined according to an instruction signal of the microcomputer 14. According to the present embodiment, the second D/A converter 28 applies the second voltage V2 to the second end portion that is the end portion of the series current 22 that is closer to the resistor 20 than the first end portion of the series current 22 is. The second D/A converter 28 is connected with a second end of the resistor 20 that is opposite to the air-fuel ratio sensor 100 through the second buffer circuit 30. The second D/A converter 28 outputs a DC voltage that is a constant voltage less than the first voltage V1, as the second voltage V2.

The second buffer circuit 30 includes an operational amplifier, and outputs a voltage from an output terminal of the second buffer circuit 30 that is the same as a voltage received by the second buffer circuit 30. The second buffer circuit 30 outputs the second voltage V2 to the first terminal 100a through the resistor 20 and the second switch 44. The second buffer circuit 30 blocks a current flowing from the resistor 20 to the second D/A converter 28. The second buffer circuit 30 is equivalent to a current blocking unit.

The amplifier circuit 32 amplifies a voltage between first and second ends of the resistor 20 and then outputs the voltage that is amplified. The amplifier circuit 32 includes an operational amplifier. The A/D converter 34 A/D converts an output of the amplifier circuit 32. The A/D converter 34 A/D converts the voltage between the first and second ends of the resistor 20 that is amplified by the amplifier circuit 32. The A/D converter 34 is equivalent to an A/D converting unit. The A/D converter 34 A/D converts the output of the amplifier circuit 32 and outputs a converting result to the microcomputer 14 at a predetermined period. According to the present embodiment, the resistor 20, the amplifier circuit 32, and the A/D converter 34 constitute a current sensing circuit 36 that is current sensing the sensor current. The current sensing circuit 36 is equivalent to a current sensing circuit unit.

The parallel circuit 38 is arranged in a parallel connection relative to the resistor 20. The parallel circuit 38 has a first end that is connected with the first end of the resistor 20, and a second end that is connected with the second end of the resistor 20. In this case, the first end of the resistor 20 is closer to the air-fuel ratio sensor 100, and the second end of the resistor 20 is closer to the second D/A converter 28. The parallel circuit 38 is equivalent to a parallel circuit unit. The parallel circuit 38 includes a first switch 40 and a constant current source 42.

The first switch 40 and the constant current source 42 are connected with each other in a series connection. When the first switch 40 is turned on or in a closed state, the second end of the resistor 20 and the constant current source 42 are in a conduction state. Thus, the constant current source 42 can supply a current to the resistor 20. The current flows in a direction along an arrow of the constant current source 42 as shown in FIG. 1. When the first switch 40 is turned off or in an open state, the second end of the resistor 20 and the constant current source 42 are electrically blocked. In this case, the resistor 20 and the constant current source 42 are in a blocking state. Thus, the constant current source 42 cannot supply the current to the resistor 20.

The second switch 44 is arranged between the resistor 20 and the air-fuel ratio sensor 100. The second switch 44 is arranged between the first end of the resistor 20 and the first terminal 100a. When the second switch 44 is turned on or in a closed state, the resistor 20 and the air-fuel ratio sensor 100 are in a conduction state. When the second switch 44 is turned off or in a closed state, the resistor 20 and the air-fuel ratio sensor 100 are electrically blocked. In this case, the resistor 20 and the air-fuel ratio sensor 100 are in a blocking state.

The microcomputer 14 includes a CPU, a ROM, a RAM, a register, and an input/output port (I/O port). In the microcomputer 14, the CPU uses a temporary storing function of the RAM or the register, and executes a signal operation based on a control program previously stored in the ROM and various datas obtained from external devices. The microcomputer 14 can output a signal obtained by the signal operation to external devices. The microcomputer 14 executes various functions. The microcomputer 14 executes an air-fuel ratio sensing control that is included in the various functions. The microcomputer 14 calculates the sensor current flowing through the air-fuel ratio sensor 100, based on the converting result of the A/D converter 34. In other words, the microcomputer 14 calculates the sensor current based on an output of the current sensing circuit 36. The microcomputer 14 calculates the air-fuel ratio based on the sensor current.

Referring to FIGS. 2 to 6, the air-fuel ratio control executed by the microcomputer 14 will be described. When an ignition switch (IG) of the vehicle is turned on and when the engine ECU 10 is energized, the microcomputer 14 starts to execute an air-fuel control shown in FIG. 2.

Figure 2:
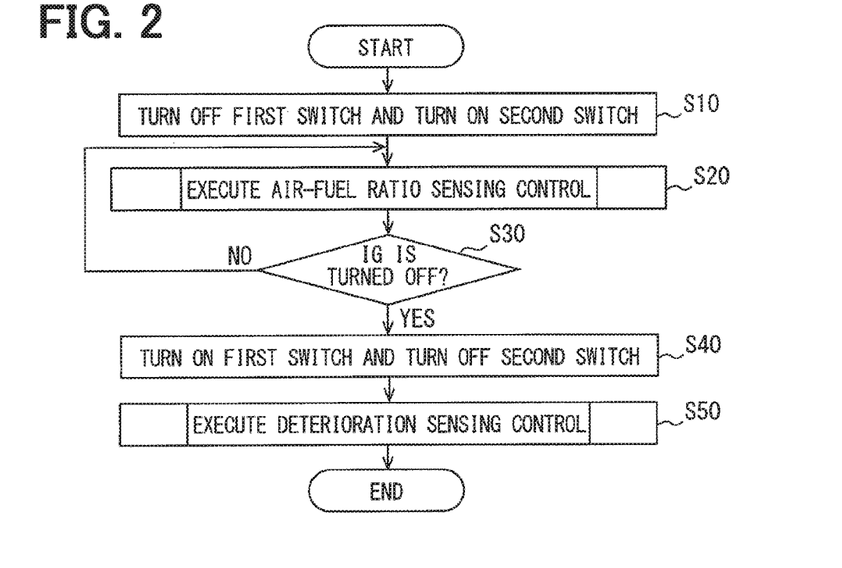
FIG. 2 is a flowchart showing an air-fuel ratio control executed by a microcomputer.

As shown in FIG. 2, at S10, the microcomputer 14 outputs an off signal to the first switch 40, and outputs an on signal to the second switch 44. Thus, the first switch 40 is turned off, and the second switch 44 is turned on.

Figure 3:
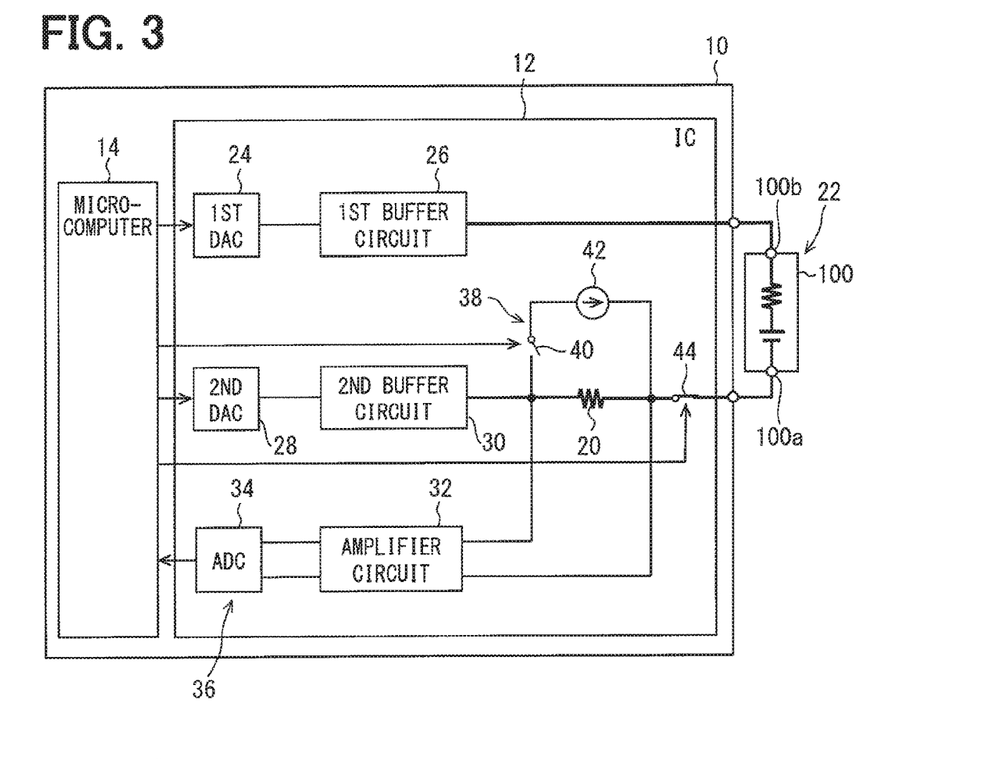
FIG. 3 is a diagram showing the engine ECU when an air-fuel ratio sensing control is executed.

As shown in FIG. 3, a current path of when the air-fuel ratio sensing control is executed is indicated after an operation in S10 is executed. The current path is a path through which a current flows. As shown in FIG. 3, the current path is indicated by a bold line. When the first switch 40 is turned off and when the second switch 44 is turned on, the current path between the first buffer circuit 26 and the second buffer circuit 30 becomes in a conduction state. That is, the current flowing through the air-fuel ratio sensor 100 flows through the resistor 20. Since the first switch 40 is turned off, the constant current source 42 does not supply a current to the resistor 20.

Figure 4:
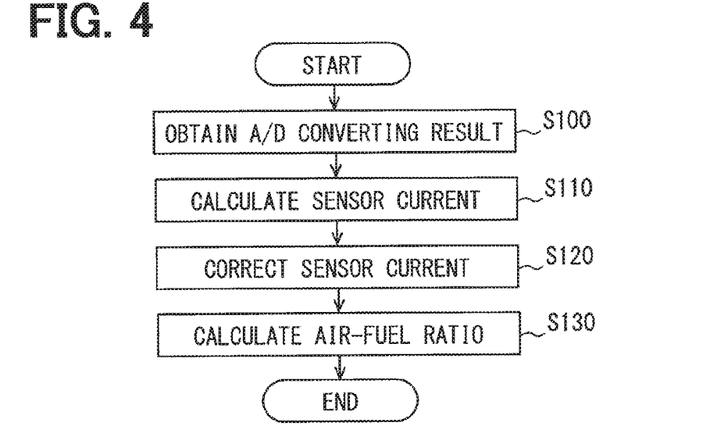
FIG. 4 is a flowchart showing the air-fuel ratio sensing control.

At S20, the microcomputer 14 executes the air-fuel ratio sensing control to sense the air-fuel ratio. An operation in S20 is equivalent to an air-fuel ratio sensing unit. FIG. 4 indicates the air-fuel ratio sensing control of S20.

As shown in FIG. 4, at S100, the microcomputer 14 obtains an A/D converting result that is the converting result of the A/D converter 34. At S110, the microcomputer 14 calculates the sensor current flowing through the air-fuel ratio sensor 100 based on an A/D converting value that is equivalent to the converting result. The microcomputer 14 calculates the sensor current based on a voltage V between the first and second ends of the resistor 20 that is the converting result of the A/D converter 34, a resistance value of the resistor 20, and a gain that is an amplifying level of the amplifier circuit 32.

When a voltage difference between the first voltage V1 and the second voltage V2 that is obtained by subtracting the second voltage V2 from the first voltage V1 is greater than an inner electromotive force of the air-fuel ratio sensor 100, the air-fuel ratio is in a lean state. In this case, the sensor current flows from the first terminal 100a toward the second terminal 100b in a positive direction. When the voltage difference is less than the inner electromotive force, the air-fuel ratio is in a rich state. In this case, the sensor current flows in a negative direction.

At S120, the microcomputer 14 corrects the sensor current calculated at S110. The microcomputer 14 corrects the sensor current by using a correction value set by a deterioration sensing control. Thus, a variation of the sensor current generated due to a deterioration of the current sensing circuit 36 such as a time deterioration is corrected. When the deterioration of the current sensing circuit 36 occurs, at least one of the resistor 20, the amplifier circuit 32, or the A/D converter 34 is deteriorated.

At S130, the microcomputer 14 calculates the air-fuel ratio based on the sensor current that is corrected. The microcomputer 14 calculates the air-fuel ratio based on a map of a function indicating a correspondence relationship between the sensor current and the air-fuel ratio. The microcomputer 14 corrects the air-fuel ratio by calculating the air-fuel ratio based on the sensor current that is corrected. When the microcomputer 14 calculates the air-fuel ratio, the microcomputer 14 terminates the air-fuel ratio sensing control, and proceeds to S30 shown in FIG. 2. The microcomputer 14 controls the air-fuel ratio of a mixture supplied to the engine at a target value, by feedback controlling a fuel injection quantity of a fuel to be injected into the engine according to the air-fuel ratio that is calculated.

At S30, the microcomputer 14 determines whether the ignition switch is turned off. When the microcomputer 14 determines that the ignition switch is turned on, the microcomputer 14 returns to S20 to repeatedly execute the air-fuel ratio sensing control. In other words, the microcomputer 14 returns to S20 to repeatedly execute the air-fuel ratio sensing control, until the microcomputer 14 determines that the ignition switch is turned off.

When the microcomputer 14 determines that the ignition switch is turned off, the microcomputer 14 proceeds to S40. At S40, the microcomputer 14 outputs an on signal to the first switch 40, and outputs an off signal to the second switch 44. Thus, the first switch 40 is turned on, and the second switch 44 is turned off. Operations in S10 and S40 are equivalent to a controlling unit.

Figure 5:
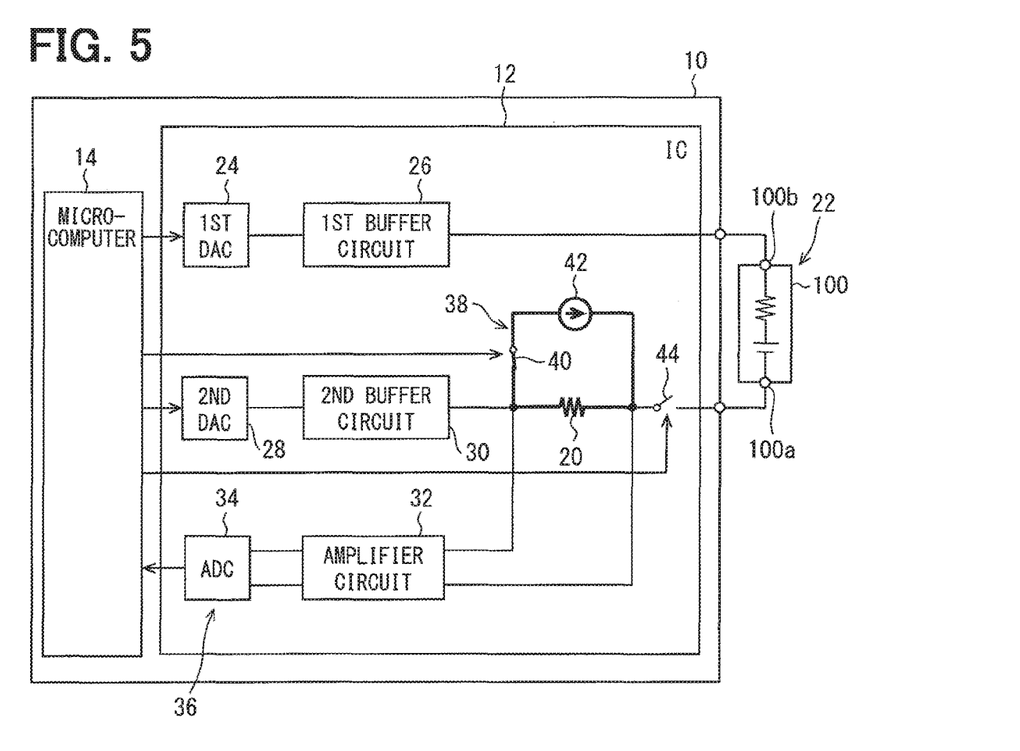
FIG. 5 is a diagram showing the engine ECU when a deterioration sensing control is executed.

As shown in FIG. 5, a current path of when the deterioration sensing control is executed is indicated after the operation in S40 is executed. As shown in FIG. 5, the current path is indicated by a bold line. When the first switch 40 is turned on and when the second switch 44 is turned off, a closed circuit constituted by the resistor 20 and the parallel circuit 38 becomes the current path. Thus, the current outputted by the constant current source 42 flows through the resistor 20, and an electrical power is consumed by the resistor 20. Since the second switch 44 is turned off, the current does not flow through the air-fuel ratio sensor 100.

Figure 6:
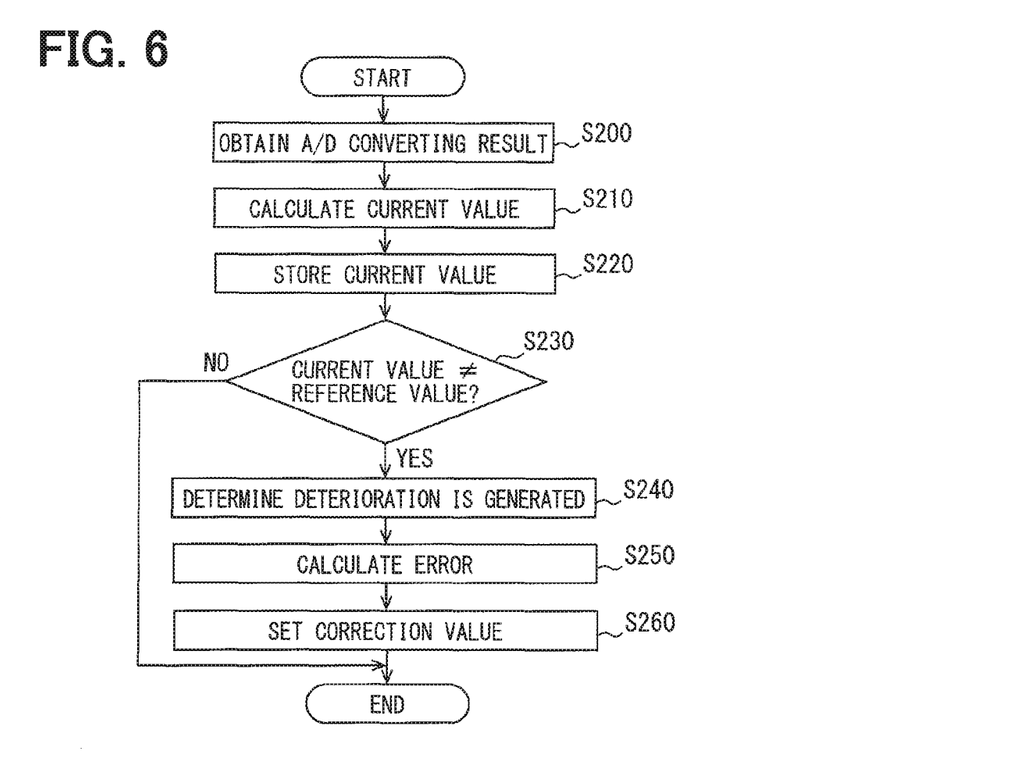
FIG. 6 is a flowchart showing the deterioration sensing control.

At S50, the microcomputer 14 executes the deterioration sensing control to sense that the current sensing circuit 36 is deteriorated. An operation in S50 is equivalent to a deterioration sensing unit. FIG. 6 indicates the deterioration sensing control of S50.

As shown in FIG. 6, at S200, the microcomputer 14 obtains the converting result of the A/D converter 34. At S210, the microcomputer 14 calculates a current value of the current flowing through the resistor 20. At S220, the microcomputer 14 stores the current value that is calculated to a memory. Similar to the sensor current, the microcomputer 14 calculates the current value based on the voltage V between the first and second ends of the resistor 20 that is the converting result of the A/D converter 34, the resistance value of the resistor 20, and the amplifying level of the amplifier circuit 32.

At S230, the microcomputer 14 compares the current value that is calculated with a reference value that is previously stored, and then determines whether the current value is different from the reference value. When the air-fuel ratio sensor 100 is being delivered from a factory, an initial correction value is set such that the microcomputer 14 can use the initial correction value to correct an error between the sensor current flowing through the air-fuel ratio sensor 100 and the sensor current that is calculated. Thus, the sensor current after being corrected when the air-fuel ratio sensor 100 is being delivered from the factory is used as the reference value. Alternatively, the correction value of the sensor current obtained at S120 may be used as the reference value. In this case, the reference value is updated every time that an operation in S120 is executed.

When the microcomputer 14 determines that the current value and the reference value are the same, the microcomputer 14 determines that the deterioration is not generated in the current sensing circuit 36, and terminates the deterioration sensing control. When the microcomputer 14 determines that the current value is different from the reference value, the microcomputer 14 proceeds to S240. At S240, the microcomputer 14 determines that the deterioration is generated in the current sensing circuit 36. At S250, the microcomputer 14 calculates the error of the current value relative to the reference value. The microcomputer 14 calculates a difference between the reference value and the current value.

At S260, the microcomputer 14 sets the correction value according to the error, and stores the correction value in a memory. In other words, the microcomputer 14 sets the correction value according to a level of the deterioration. The microcomputer 14 sets the correction value to a value where the current value approaches the reference value. Further, it is preferable that the microcomputer 14 sets the correction value to a value where the error is zero. A magnitude of the error indicates the level of the deterioration. The microcomputer 14 sets the correction value based on a map or a function indicating a correspondence relationship between the correction value and the error. The correction value that is stored is used in a next air-fuel ratio sensing control. Then, the microcomputer 14 terminates the present control.

When the deterioration sensing control in S50 is completed, the microcomputer 14 terminates the air-fuel ratio control as shown in FIG. 2.

Next, effects of the air-fuel ratio sensing device according to the present embodiment will be described.

According to the present embodiment, the IC 12 includes the parallel circuit 38 that is arranged in a parallel connection relative to the resistor 20, and the second switch 44 that is arranged between the resistor 20 and the air-fuel ratio sensor 100. The parallel circuit 38 includes the first switch 40 and the constant current source 42. In a first interval where the air-fuel ratio sensing control is executed, the first switch 40 is turned off, and the second switch 44 is turned on. In a second interval where the deterioration sensing control is executed, the first switch 40 is turned on, and the second switch 44 is turned off.

Thus, when the deterioration sensing control is executed, the constant current source 42 is electrically connected with the resistor 20, and a constant current flows through the resistor 20. When none of the resistor 20, the amplifier circuit 32, and the A/D converter 34 that constitute the current sensing circuit 36 is deteriorated, the converting result of the A/D converter 34 obtained at S200 and the current value calculated at S210 are maintained. Thus, the deterioration of the current sensing circuit 36 can be sensed by comparing a value obtained based on the converting result of the A/D converter 34 with the reference value.

Thus, it can be suppressed that the air-fuel ratio of the mixture is shifted relative to a target value in a long term when the deterioration is ignored. In other words, it can be suppressed that an environment load increases in a long term.

According to the present embodiment, the microcomputer 14 sets the correction value according to the error between the current value and the reference value when the deterioration sensing control is executed, corrects the sensor current and the air-fuel ratio, by using the correction value set in the air-fuel ratio sensing control is executed. Since the microcomputer 14 corrects the air-fuel ratio when the microcomputer 14 senses the deterioration, it can be suppressed that a performance of a sensing of the air-fuel ratio is decreased due to the deterioration. According to the present embodiment, the microcomputer 14 sets the correction value depending on the level of the deterioration. Thus, when the deterioration is generated, the air-fuel ratio sensing device can accurately maintain the performance of the sensing of the air-fuel ratio.

According to the present embodiment, the second buffer circuit 30 is used as the current blocking unit. Thus, it can be suppressed that the current flows from the resistor 20 into the second D/A converter 28, and a configuration of the IC 12 can be simplified.

According to the present embodiment, when a control is completed by the engine ECU 10, the deterioration sensing control is executed. In other words, when the air-fuel ratio control is completed by the air-fuel ratio sensing device, the deterioration sensing control is executed. Thus, the deterioration can be sensed at a regular interval, without affecting the air-fuel ratio control of the mixture. Thus, when the deterioration is generated, the deterioration can be immediately sensed.

Figure 7:
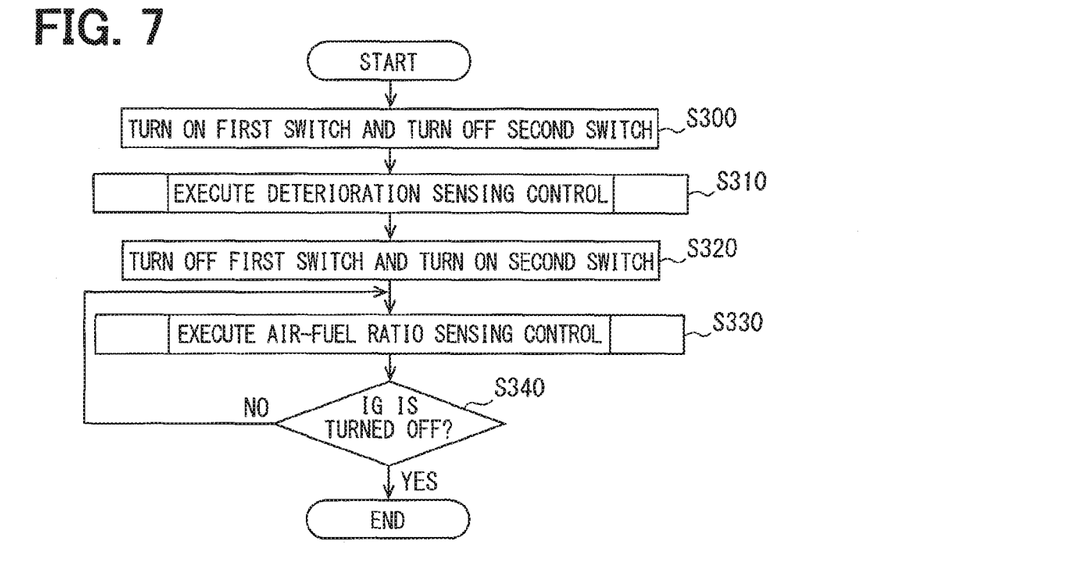
FIG. 7 is a flowchart showing an air-fuel ratio control according to a modification example.

According to a modification example shown in FIG. 7, the same effects can be obtained when the deterioration sensing control is executed in a case where the engine ECU 10 that is the air-fuel ratio sensing device is activated and the air-fuel ratio control starts. As shown in FIG. 7, at S300, the microcomputer 14 outputs the on signal to the first switch 40, and outputs the off signal to the second switch 44. Thus, the first switch 40 is turned on, and the second switch 44 is turned off. Thus, the current path shown in FIG. 5 is established. At S310, the microcomputer 14 executes the deterioration sensing control. An operation in S310 is equivalent to the operation in S50. The operation in S310 is equivalent to the deterioration sensing unit.

When the deterioration sensing control is completed, at S320, the microcomputer 14 outputs the off signal to the first switch 40, and outputs the on signal to the second switch 44. Thus, the first switch 40 is turned off, and the second switch 44 is turned on. Thus, the current path shown in FIG. 3 is established. At S330, the microcomputer 14 executes the air-fuel ratio sensing control. An operation in S330 is equivalent to the operation in S20. At S340, the microcomputer 14 repeatedly returns to execute the air-fuel ratio sensing control, until the ignition switch is turned off. When the microcomputer 14 determines that the ignition switch is turned off, the microcomputer 14 terminates the air-fuel ratio control. Operations in S300 and S320 are equivalent to the controlling unit. The operation in S330 is equivalent to the air-fuel ratio sensing unit.

Second Embodiment

A second embodiment of the present disclosure can refer to the prior embodiment. Descriptions of a common part of the engine ECU 10 that is the air-fuel ratio sensing device mentioned in the prior embodiment will be omitted.

Figure 8:
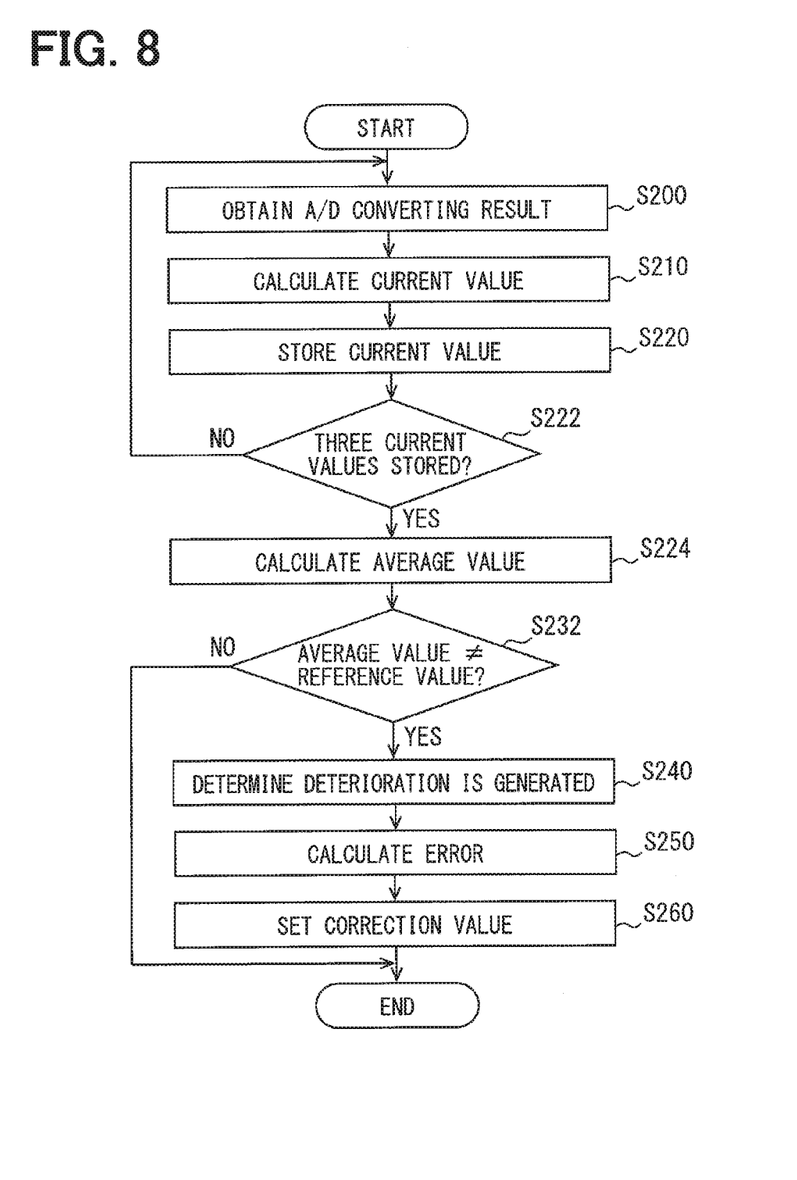
FIG. 8 is a flowchart showing the deterioration sensing control in the engine ECU to which the air-fuel ratio sensing device is applied, according to a second embodiment of the present disclosure.

According to the present embodiment, the microcomputer 14 obtains the converting result of the A/D converter 34 for plural times and senses the deterioration, in the deterioration sensing control. FIG. 8 indicates an example of the microcomputer 14 according to the present embodiment. As shown in FIG. 8, the deterioration sensing control has operations the same as that shown in FIG. 6 with the same reference numerals. Hereafter, different parts between the deterioration sensing control shown in FIG. 8 and the deterioration sensing control shown in FIG. 6 will be described.

As shown in FIG. 8, when an operation in S220 is completed, at S222, the microcomputer 14 determines whether three current values are stored since the deterioration sensing control starts. The microcomputer 14 repeatedly executes operations in S200 to S220, until the three current values are stored.

When the microcomputer 14 determines that the three current values are stored at S222, the microcomputer 14 proceeds to S224. At S224, the microcomputer 14 calculates an average value of the three current values. At S232, the microcomputer 14 determines whether the average value that is calculated is different from the reference value. When the microcomputer 14 determines that the average value and the reference value are the same, the microcomputer 14 terminates the present control. When the microcomputer 14 determines that the average value is different from the reference value, the microcomputer 14 executes operations in and after S240 as the same as that shown in FIG. 6.

According to the present embodiment, since the deterioration is sensed based on plural converting results, it can be suppressed that an erroneous sensing of the deterioration is generated due to a noise.

According to the present embodiment, a sensing number of the current values is not limited to three. The sensing number may be a value greater than three. A comparison between the average value and the reference value is not limited to a case where the average value is obtained by using all of the current values. For example, when one of the three current values is remarkably different from the other two of the three current values, the average value can be calculated only based on the other two of the three current values, and then the comparison is executed.

Third Embodiment

A third embodiment of the present disclosure can refer to the prior embodiments. Descriptions of a common part of the engine ECU 10 that is the air-fuel ratio sensing device mentioned in the prior embodiments will be omitted.

Figure 9:
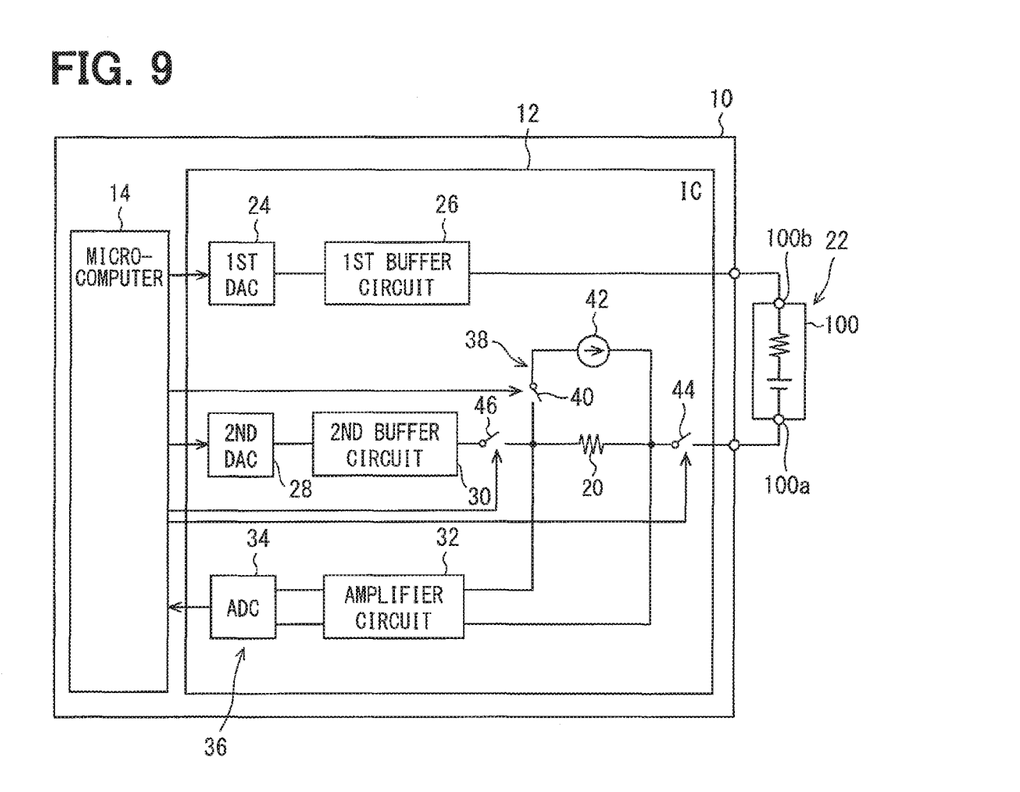
FIG. 9 is a diagram showing the engine ECU to which the air-fuel ratio sensing device is applied, according to a third embodiment of the present disclosure.

According to the present embodiment, as shown in FIG. 9, the IC 12 includes a third switch 46 that is equivalent to the current blocking unit. The third switch 46 is arranged between the first end of the resistor 20 and the second buffer circuit 30. The third switch 46 is turned on and turned off as the same as the second switch 44. The microcomputer 14 controls to turn on the second switch 44 and the third switch 46 in a case where the air-fuel ratio sensing control is executed. The microcomputer 14 controls to turn off the second switch 44 and the third switch 46 in a case where the deterioration sensing control is executed.

According to the present embodiment, the above configuration is used, and effects the same as that in the prior embodiments can be obtained.

The present disclosure is not limited to the above embodiments. The present disclosure is intended to cover various modification and equivalent arrangements including the above embodiments. The present disclosure is not limited to combinations of parts or components mentioned in the above embodiments. The present disclosure can be applied to various combinations. The scope of the present disclosure is not limited to the above embodiments. In addition, while the various combinations and configurations, which are preferred, other combinations and configurations, including more, less or only a single element, are also within the spirit and scope of the present disclosure.

The voltages applied to the air-fuel ratio sensor 100 are not limited to the above embodiments. The first voltage V1 may be a DC voltage that varies according to the sensor current. The second voltage V2 may be an AC voltage. Alternatively, the second voltage V2 may include two voltages that are a first-level voltage and a second-level voltage and are periodically switched to each other. When the second voltage is the AC voltage or is switched between the above two voltages, an impedance of the air-fuel ratio sensor 100 can be sensed. Since the impedance is a value correlative to a temperature of the air-fuel ratio sensor 100, the microcomputer 14 determines an active state of the air-fuel ratio sensor 100 based on the impedance that is calculated and can control a heater that is not shown and heats the air-fuel ratio sensor 100.

According to the above embodiments, the resistor 20 is arranged between the second D/A converter 28 and the first terminal 100a of the air-fuel ratio sensor 100 that is the negative terminal of the air-fuel ratio sensor 100. However, the resistor 20 may be arranged between the first D/A converter 24 and the second terminal 100b of the air-fuel ratio sensor 100 that is the positive terminal of the air-fuel ratio sensor 100. In this case, the parallel circuit 38 and the second switch 44 are also arranged to be close to the positive terminal of the air-fuel ratio sensor 100. In other words, the parallel circuit 38 and the second switch 44 are connected with the second terminal 100b of the air-fuel ratio sensor 100.

According to the above embodiments, the current sensing circuit 36 is constituted by the resistor 20, the amplifier circuit 32, and the A/D converter 34. However, the current sensing circuit 36 may at least include the resistor 20 and the A/D converter 34. According to the above embodiments, the amplifier circuit 32 includes the amplifier. However, the amplifier circuit 32 may have components to achieve an amplification without the amplifier.

According to the above embodiments, a predetermined value is used as the reference value in S230 and S232. However, the reference value may be a range. According to the above embodiments, the current value calculated from the converting result is used to be compared with the reference value. However, a value obtained based on the converting result of the A/D converter 34 may be used to be compared with the reference value. For example, the microcomputer 14 may compare the converting result with the reference value that corresponds to the converting result.

According to the above embodiments, the microcomputer 14 is equivalent to the controlling unit, the air-fuel ratio sensing unit, and the deterioration sensing unit. However, the controlling unit, the air-fuel ratio sensing unit, and the deterioration sensing unit may be provided by a software stored in a memory device that is substantive and a computer executing the software, only by a software, only by a hardware, or by a combination of the above components. When the controlling unit, the air-fuel ratio sensing unit, and the deterioration sensing unit are provided by an electric circuit that is a hardware, the controlling unit, the air-fuel ratio sensing unit, and the deterioration sensing unit are provided by a digital circuit including logic circuits or by an analog circuit.

According to the above embodiments, when the deterioration is determined in the deterioration sensing control, the correction value is set according to the error between the current value and the reference value. However, the correction value may be cancelled. When the deterioration is determined, the microcomputer 14 may control a communication device including an indicator lamp or an interior monitor to make a user know that the deterioration is generated.

While the present disclosure has been described with reference to the embodiments thereof, it is to be understood that the disclosure is not limited to the embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. An air-fuel ratio sensing device comprising:
a resistor connected with an air-fuel ratio sensor in a series connection, the resistor and the air-fuel ratio sensor constituting a series circuit, the series circuit having a first end portion and a second end portion;
an A/D converter A/D converting a voltage between two ends of the resistor, the A/D converter and the resistor constituting a current sensing circuit unit;
a parallel circuit unit connected with the resistor in a parallel connection, the parallel circuit unit including a first switch and a constant current source which are connected with each other in a series connection;
a second switch arranged between the resistor and the air-fuel ratio sensor;
a controlling unit controlling to turn off the first switch to make the constant current source and the resistor be in a blocking state and controlling to turn on the second switch to make the resistor and the air-fuel ratio sensor be in a conduction state in a first interval, the controlling unit controlling to turn on the first switch to make the constant current source and the resistor be in a conduction state and controlling to turn off the second switch to make the resistor and the air-fuel ratio sensor be in a blocking state in a second interval that is different from the first interval;
an air-fuel ratio sensing unit sensing an air-fuel ratio based on a converting result of the A/D converter in the first interval; and
a deterioration sensing unit comparing a reference value that is previously stored with a value obtained based on the converting result of the A/D converter and sensing a deterioration generated in the current sensing circuit unit in the second interval.

2. The air-fuel ratio sensing device according to claim 1, wherein
the deterioration sensing unit sets a correction value used to correct the air-fuel ratio depending on a level of the deterioration, and
the air-fuel ratio sensing unit corrects the air-fuel ratio by using the correction value.

3. The air-fuel ratio sensing device according to claim 1, wherein
the deterioration sensing unit obtains the converting result of the A/D converter for plural times and senses the deterioration in the second interval.

4. The air-fuel ratio sensing device according to claim 1, wherein
the second interval is set when the air-fuel ratio sensing device is activated or when a control of the air-fuel ratio sensing device is completed.

5. The air-fuel ratio sensing device according to claim 1, further comprising:
a first voltage applying unit applying a first voltage to the first end portion of the series circuit;
a second voltage applying unit applying a second voltage different from the first voltage to the second end portion of the series circuit; and
a current blocking unit arranged between an end portion of the series circuit that is closer to the resistor than the other end portion of the series circuit is and a voltage applying unit that is one of the first voltage applying unit and the second voltage applying unit and applies a voltage to the end portion of the series circuit, the current blocking unit blocking a current flowing from the resistor to the voltage applying unit.

6. The air-fuel ratio sensing device according to claim 5, wherein
the current blocking unit is a buffer circuit unit.

7. The air-fuel ratio sensing device according to claim 5, wherein
the current blocking unit is a third switch, and
the controlling unit controls to turn on the third switch in the first interval and controls to turn off the third switch in the second interval.

* * * * *